United States Patent [19]

Liu et al.

[11] Patent Number: 5,626,836
[45] Date of Patent: May 6, 1997

[54] LOW VOC HAIR SPRAY COMPOSITIONS CONTAINING TERPOLYMERS OF VINYL PYRROLIDONE, VINYL CAPROLACTAM AND 3-(N-DIMETHYLAMINOPROPYL) METHACRYLAMIDE

[75] Inventors: Kou-Chang Liu, Wayne; Colleen M. Rocafort, Lake Hiawatha; Lowell R. Anderson, Morristown.; Yakir Reuven, West Orange, all of N.J.

[73] Assignee: ISP Investments Inc., Wilmington, Del.

[21] Appl. No.: 365,259

[22] Filed: Dec. 28, 1994

[51] Int. Cl.⁶ .................................................. A61K 7/11
[52] U.S. Cl. .................... 424/47; 424/78.02; 424/70.11; 424/DIG. 1; 424/DIG. 2; 514/957; 526/264; 526/307; 526/307.3
[58] Field of Search .................... 424/47, DIG. 1, 424/DIG. 2, 780.2, 70.1; 514/957; 526/264, 307, 307.3

[56] References Cited

U.S. PATENT DOCUMENTS

| | | | |
|---|---|---|---|
| 5,126,124 | 6/1992 | Tazi et al. | 424/47 |
| 5,158,762 | 10/1992 | Pierce | 424/47 |
| 5,275,809 | 1/1994 | Chen et al. | 424/70.11 |

*Primary Examiner*—Raj Bawa
*Attorney, Agent, or Firm*—Walter Katz; Marilyn J. Maue; Joshua J. Ward

[57] ABSTRACT

Low VOC hair spray resin compositions containing homogeneous terpolymers of vinyl pyrrolidone, vinyl caprolactam and 3-(N-dimethylaminopropyl) methacrylamide are described. The hair spray compositions are made using a solution of the terpolymer which is clear and low in viscosity, and which provides a spray of relative small particle size. The hair spray compositions exhibit an effective high humidity curl retention property.

17 Claims, 2 Drawing Sheets

LOW VOC HAIR SPRAY COMPOSITIONS CONTAINING TERPOLYMERS OF VINYL PYRROLIDONE, VINYL CAPROLACTAM AND 3-(N-DIMETHYLAMINOPROPYL) METHACRYLAMIDE

BACKGROUND OF THE INVENTION

1. Field of the Invention

This invention relates to low VOC hair spray resin compositions, and, more particularly, to substantially homogeneous terpolymers of vinyl pyrrolidone (VP), vinyl caprolactam (VCL) and 3-(dimethylaminopropyl) methacrylamide (DMAPMA) as the hair fixative therein.

2. Description of the Prior Art

U.S. Pat. No. 5,158,762 disclosed hair spray compositions containing terpolymers obtained by one-pot polymerization of vinyl pyrrolidone, vinyl caprolactam and dimethylaminoethyl methacrylate (DMAEMA) (e.g. GAFFIX® VC-713, supplied by International Specialty Products). The monomer 3-(N-dimethylaminopropyl) methacrylamide was considered as a suitable ammonium derivative to replace dimethylaminoethyl methacrylate in the terpolymer, however without further description.

Accordingly, it is an object of this invention to provide a solution of a substantially homogeneous terpolymer of VP, VCL and DMAPMA monomers, in a defined composition, which is clear and low in viscosity, which forms a spray of relatively small particle size, and is an effective fixative resin for a 55% VOC hair spray composition having effective curl retention properties.

Another object of the invention is to provide a clear, low viscosity solution of a substantially homogeneous terpolymer of VP, VCL and DMAPMA, in a predetermined composition, which is made by a homogeneous polymerization process.

DEFINITIONS (1) The active fixative resin of the invention is a substantially homogeneous terpolymer of 1–20 wt. %, preferably 5–15 wt. %, of vinyl pyrrolidone (VP), 60–95 wt. %, preferably 80–90 wt. %, of vinyl caprolactam (VCL) and 1–10 wt. %, preferably 2.5–7.5 wt. %, of 3-(N-dimethylaminopropyl) methacrylamide (DMAPMA), which is made by a process of homogeneous polymerization.

(2) The homogeneous polymerization process of the invention comprises precharging VCL in a reactor, optionally with a predetermined small amount of VP and/or DMAPMA, suitably less than 15%, and introducing VP and DMAPMA incrementally into the reactor at a predetermined feeding schedule so that the rate of disappearance of both VP and DMAPMA substantially coincides with the rate of disappearance of VCL during the polymerization.

(3) The hair spray concentrate of the invention is the homogeneous terpolymer resin in an aqueous, aqueous-alcoholic or alcoholic solvent wherein the concentration of the terpolymer is between about 10 and about 70 wt. %, preferably 35–55 wt. %.

(4) The 55% VOC (volatile organic compounds) pump spray composition of the invention is a solution or suspension of the homogeneous terpolymer containing 1–10% solids, preferably 3–5% solids, in 55% or less alcohol, preferably ethanol, the rest water and adjuvants, preferably including a corrosion inhibitor.

(5) The 55% VOC aerosol hair spray composition is the 1–10% solids, preferably 2–4% solids, composition of the homogeneous terpolymer with 20 wt. % or less alcohol, preferably ethanol, and 35 wt. % or less of propellant, preferably dimethyl ether (DME), and a neutralizer and other adjuvants, preferably including a corrosion inhibitor.

SUMMARY OF THE INVENTION

In accordance with the invention, there is provided herein:

A. An improved hair fixative resin which is a substantially homogeneous terpolymer comprising, by weight, 1–20%, preferably 5–15%, of VP; 60–95%, preferably 80–90%, of VCL; and 1–10%, preferably 2.5–7.5%, of DMAPMA.

B. A homogeneous polymerization process for making the homogeneous terpolymer of the invention. In this process the slowest reacting monomer of the terpolymer (VCL) is precharged, optionally with small amounts of VP and DMAPMA, and the faster reacting monomers (VP and DMAPMA) are introduced incrementally into the reactor at a predetermined feeding schedule so that the rate of disappearance of VP and DMAPMA monomers substantially matches the rate of disappearance of VCL during the polymerization.

C. A solution of the substantially homogeneous terpolymer of the invention which is crystal clear (Hach value of less than 10 NTU, preferably less than 1 NTU), and has a low viscosity (less than 300,000 cps, preferably less than 100,000 cps).

D. A 55% VOC hair spray resin composition containing 2–10 wt. % of the homogeneous terpolymer having an effective spray pattern, a particle size of 85 microns, and a desirable high humidity curl retention property.

IN THE DRAWINGS

DETAILED DESCRIPTION OF THE INVENTION

Determination of Addition Schedules for VP and DMAPMA to Form a Homogeneous Terpolymer with VCL A. First, a one-pot polymerization of VCL, VP and DMAPMA monomers was carried out as follows:

EXAMPLE 1

Vinyl caprolactam (591.43 g), vinyl pyrrolidone (55.57 g), dimethylaminopropyl methacrylamide (DMAPMA) (42.56 g) and ethanol (842.8 g) were charged into a 2-liter water-jacketed resin flask. The reaction flask was equipped with a condenser, a thermometer, a septum (for catalyst addition), an anchor type metal stirrer, and a nitrogen sparge tube. Nitrogen was bubbled through the solution while the resin flask was heated using hot water circulating through the jacketed flask. After the temperature of the solution reached 68° C., an additional half-hour was allowed before the first Lupersol 11 (0.25 ml) was injected into the flask. Subsequently, Lupersol 11 additions were made at 10, 40, 70, 100, 140 and 180 minutes after the first addition. The reaction temperature was brought up to 74° C. and two shots of Lupersol 554 M75 (0.25 ml) were added at 240 and 330 minutes. The contents were allowed to react for an additional five hours at 74° C. and then cooled to 35°–40° C. After being neutralized with 12.25 g of concentrated sulfuric acid, the product was discharged.

The relative percentage amounts of residual monomers present during the course of the one-pot reaction was determined by gas chromatographic analysis after sampling the reaction mixture periodically. The analytical data obtained then was plotted as the graph of FIG. 1.

Figure 1:
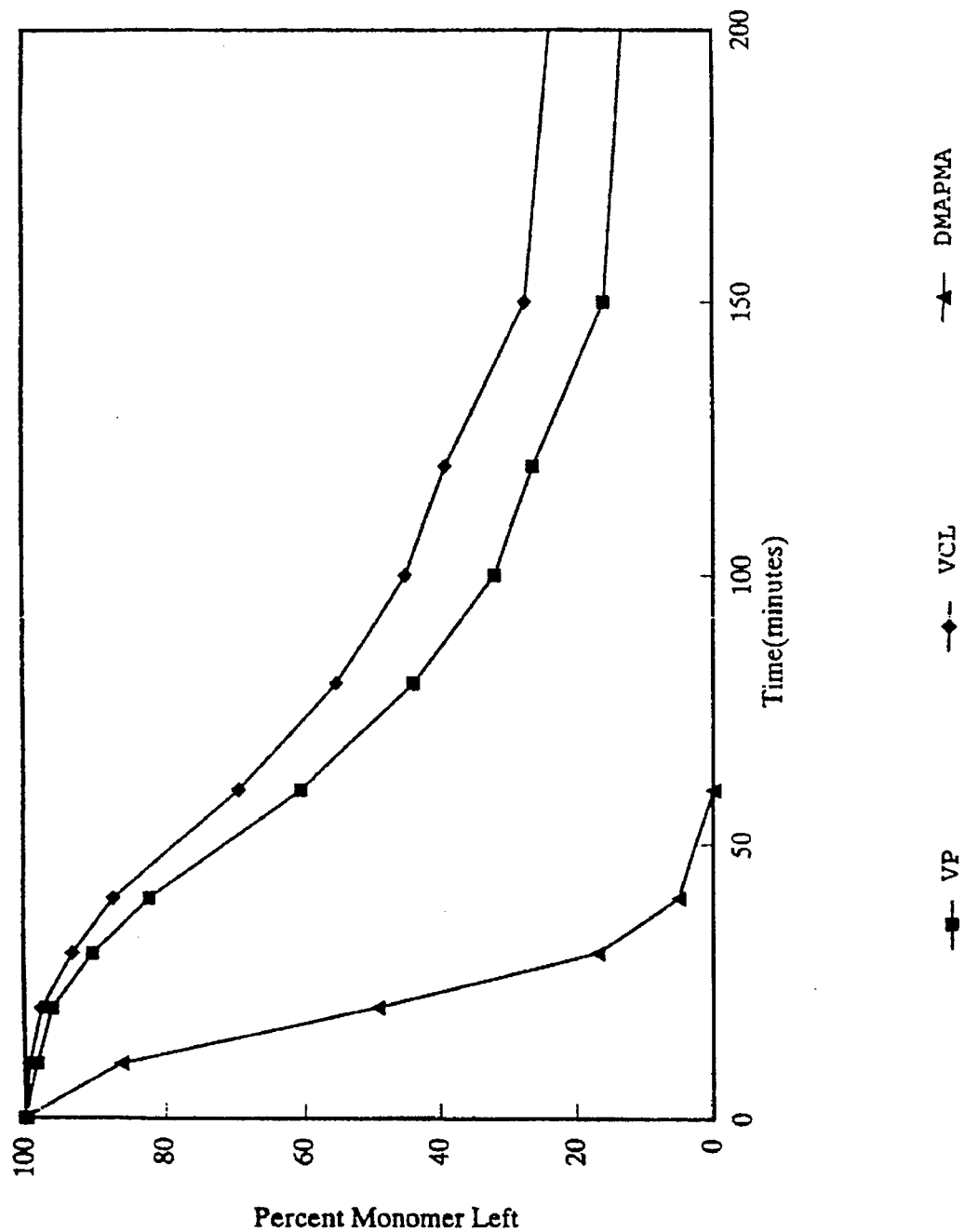
FIG. 1 is a graphical representation of a non-homogeneous (one-pot) polymerization process in which is plotted percent unreacted vinyl caprolactam (VCL), vinyl pyrrolidone (VP) and dimethylaminopropyl methacrylamide (DMAPMA) vs. time for a reaction mixture of Example 1 below.

As shown in FIG. 1, the VP and DMAPMA monomers react much more rapidly than VCL. Accordingly, after 100 minutes, for example, all the VP and DMAPMA monomers are consumed while residual VCL monomer still is available for homopolymerization. Thus the terpolymer formed is of a composition different from the desired monomer ratios selected by the precharged amounts of the two monomers. Under these experimental conditions, the polymer product obtained is a complex mixture of a homopolymer which is polyvinyl caprolactam, various copolymers, and a terpolymer of VCL, VP and DMAPMA of uncertain composition.

B. To form a homogeneous terpolymer, it is necessary that the curve of rate of reaction vs. time for both VP and DMAPMA substantially coincide or match the rate of reaction curve for VCL. To accomplish this, the VCL is precharged and substantially all the VP and DMAPMA monomers are fed external to the precharge at a feeding schedule determined by analysis of the data of FIG. 1. The % VP and DMAPMA monomers to be fed at time t of the polymerization is determined from the Asymmetric Double Sigmoidal Distribution formula, $A_t$, below, which has four adjustable parameters, $a_1$, $a_2$, $a_3$ and $a_4$:

$$A_t = \frac{1}{1+\exp\left[\frac{a_1 - \frac{a_2}{2} - t}{a_3}\right]} \left[1 - \frac{1}{1+\exp\left[\frac{a_1 + \frac{a_2}{2} - t}{a_4}\right]}\right]$$

where t=time in minutes during copolymerization;

$a_1$ is a parameter which determines the center of the distribution;

$a_2$ is a parameter which affects the width of the distribution;

$a_3$ is a parameter which determines the ascending portion of the distribution; and $a_4$ is a parameter which determines the descending portion of the distribution.

$$\% \text{ VP or DMAPMA to be fed at time } t = \frac{A_t}{\sum_{t=0}^{N} A_t} \times 100$$

where N=time when the polymerization is completed.

To match the VP and DMAPMA curves to the VP curve of FIG. 1, an "initial guess" is made for the values of $a_1$, $a_2$, $a_3$ and $a_4$ for each of these monomers. Then these values are inserted into the $A_t$ formula and the % VP and DMAPMA to be fed at time t is calculated. The resulting % unreacted VP and DMAPMA during this polymerization will probably not match the % unreacted VP at the same time t. If the % unreacted VP or DMAPMA at time t is too large, then the value of $a_3$ (ascendency) in the $A_t$ formula is increased, $a_4$ (descendency) is decreased, $a_1$ (center) is decreased, and $a_2$ (width) is decreased. Conversely, if the initial guess values of $a_1$ through $a_4$ give a reaction rate for VP or DMAPMA which is too fast, then changes in the values of $a_1$ through $a_4$ are made in a direction opposite to those discussed above.

These new values of the parameters are then used to determine a new feeding schedule. Using this feeding schedule, another polymerization is carried out, and the process of adjustment of the parameters described above is repeated.

This process is known as "interative fitting" of data to a curve. After 4 or 5 such iterative fittings, the experimental VCL, VP and DMAPMA curves will be matched, as shown in FIG. 2 herein.

Figure 2:
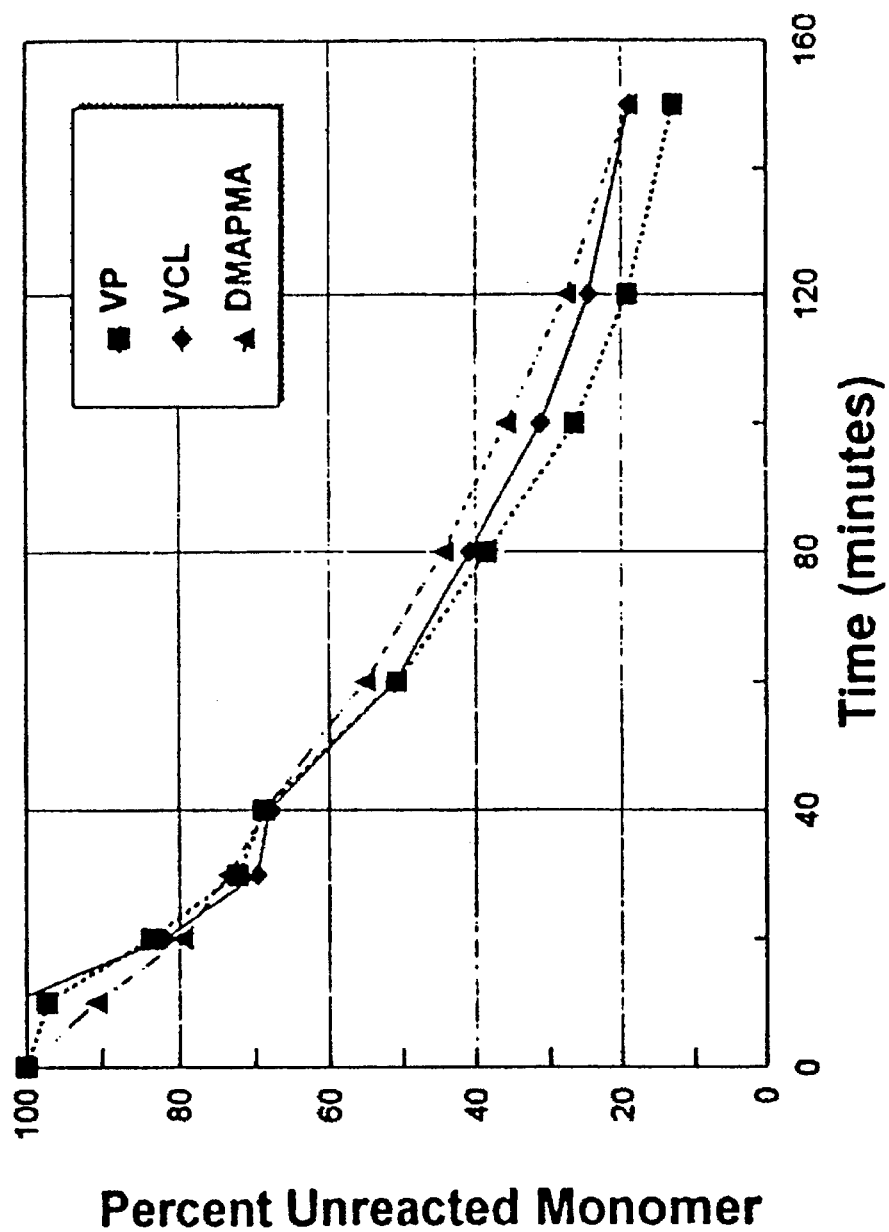
FIG. 2 is a similar plot as FIG. 1 for the homogeneous process of the invention according to Example 2 below.

The matched curves of VCL, VP and DMAPMA in FIG. 2 will have at least one set of values for $a_1$, $a_2$, $a_3$ and $a_4$ (the last set of the iterative fitting process) for suitable feeding of VP and DMAPMA over the entire period of polymerization. One such set is:

| VP | DMAPMA |
|---|---|
| $a_1 = 1$ | $a_1 = 32$ |
| $a_2 = 10$ | $a_2 = 50$ |
| $a_3 = 1$ | $a_3 = 15$ |
| $a_4 = 30$ | $a_4 = 75$ |

C. With such schedules available, a homogeneous terpolymer of VCL, VP, and DMAPMA can be prepared as described in Example 2 below.

EXAMPLE 2

Preparation of a Homogeneous Terpolymer of 85% VCL, 10% VP and 5% DMAPMA

Vinyl caprolactam (VCL) (602.1 g—100%), vinyl pyrrolidone (28.1 g—50.4%), DMAPMA (4.38 g—10.1%) and ethanol (858 g) (45% solids) were charged into a 2-liter resin pot equipped with a gas inlet, a liquid inlet, a thermometer and a condenser. The pH of the solution was adjusted to about 7.5 with KOH. Then a stream of nitrogen is introduced which bubbles through the solution during the reaction. The solution was gradually heated to 65° C. Then VP (63.2 g) and DMAPMA (51.4 g) were introduced incrementally into the pot with vigorous stirring over a period of 5 hours so that the relative concentrations of the monomeric VCL, VP and DMAPMA monomer remained practically constant throughout the reaction at predetermined levels.

As soon as VP and DMAPMA are introduced to the pot, Lupersol 11 (t-butylperoxy pivalate in mineral spirits) catalyst is added. The rate of the addition of the catalyst is such that 2 ml of Lupersol is completely delivered in 4 hours. The solution is held for an additional 3 hours at the 68° C. The product is an alcoholic solution of the homogeneous terpolymer of VCL, VP and DMAPMA.

180 g of the polymer solution then was transferred to a 2-liter flask and 500 g of distilled water was added. The resulting solution then was stripped under reduced pressure at 40°–50° C. on a rotovap to remove 200 g of solvent (ethanol/water). A clear viscous polymer solution in water was obtained.

The sequence and mode of addition of monomers during the process is summarized in Table 1 below and the plot in FIG. 2.

TABLE 1

FEEDING SCHEDULE FOR EXAMPLE 2
Charge 45% solids in ethanol,
VP/DMAPMA//VCL = 10/5/85 (% mole)
Asymmetric Double Sigmoidal Distribution
VP (1, 10, 1, 30), DMAPMA (32, 50, 15, 75)

| Time (min) | VP (ml) | DMAPMA (ml) | VCL (gr) | EtOH (gr) | Total (gr) |
|---|---|---|---|---|---|
| 0 | 27.42 | 4.71 | 602.11 | 858.00 | 1493.02 |
| 0–30 | 15.74 | 8.69 | 0 | 0 | 1517.50 |
| 30–60 | 7.20 | 8.54 | 0 | 0 | 1532.95 |
| 60–90 | 2.91 | 7.00 | 0 | 0 | 1542.51 |
| 90–120 | 1.11 | 5.40 | 0 | 0 | 1548.71 |
| 120–150 | 0.00 | 4.02 | 0 | 0 | 1552.46 |
| 150–180 | 0.00 | 2.91 | 0 | 0 | 1555.18 |
| 180–210 | 0.00 | 2.06 | 0 | 0 | 1557.10 |
| 210–240 | 0.00 | 1.44 | 0 | 0 | 1558.45 |
| 240–270 | 0.00 | 0.99 | 0 | 0 | 1559.37 |
| 270–300 | 0.00 | 0.68 | 0 | 0 | 1560.00 |
| Total (gr) | 56.56 | 43.33 | 602.11 | 858 | 1560 |
| % Wt | 3.63 | 2.78 | 38.60 | 55.00 | 100 |
| % wt (t = 0) | 1.91 | 0.29 | 40.33 | 57.47 | 100 |

Density : VP: 1.04 g/ml
DMAPMA : 0.933 g/ml

EXAMPLE 3

Preparation of a Homogeneous Terpolymer of 55% VCL, 40% VP and 5% DMAPMA

Vinyl caprolactam (VCL) (414.9 g—100%), vinyl pyrrolidone (1065 g—44.2%), DMAPMA (0.67 g—1.5%) and ethanol (858 g) were charged into a 2-liter resin pot equipped with a gas inlet, a liquid inlet, a thermometer and a condenser. The pH of the solution was adjusted to about 7.5 with KOH. Then a stream of nitrogen is introduced which bubbles through the solution during the reaction. The solution was gradually heated to 65° C. Then VP (63.2 g) and DMAPMA (51.4 g) were introduced incrementally into the pot with vigorous stirring over a period of 5 hours so that the relative concentrations of the monomeric VCL, VP and DMAPMA monomer remained practically constant throughout the reaction at predetermined levels.

As soon as VP and DMAPMA are introduced to the pot, Lupersol 11 (t-butylperoxy pivalate in mineral spirits) catalyst is added. The rate of the addition of the catalyst is such that 2 ml of Lupersol is completely delivered in 4 hours. The solution is held for an additional 3 hours at the 68° C. The product is an alcoholic solution of the homogeneous terpolymer of VCL, VP and DMAPMA.

TABLE 2

FEEDING SCHEDULE FOR EXAMPLE 3
Charge 45% solids in ethanol,
VP/DMAPMA/VCL = 40/5/55 (% mole)
Asymmetric Double Sigmoidal Distribution
VP (1, 7, 1, 34), DMAPMA (40, 20, 10, 80)

| Time (min) | VP (ml) | DMAPMA (ml) | VCL (gr) | EtOH (gr) | Total (gr) |
|---|---|---|---|---|---|
| 0 | 103.95 | 0.72 | 414.92 | 858.00 | 1381.70 |
| 0–30 | 67.70 | 6.55 | 0 | 0 | 1458.22 |
| 30–60 | 34.50 | 10.40 | 0 | 0 | 1503.81 |
| 60–90 | 15.79 | 8.77 | 0 | 0 | 1528.42 |
| 90–120 | 6.83 | 6.85 | 0 | 0 | 1541.92 |
| 120–150 | 2.88 | 5.19 | 0 | 0 | 1549.76 |
| 150–180 | 0.00 | 3.83 | 0 | 0 | 1553.34 |
| 180–210 | 0.00 | 2.78 | 0 | 0 | 1556.93 |
| 210–240 | 0.00 | 1.98 | 0 | 0 | 1557.78 |
| 240–270 | 0.00 | 1.40 | 0 | 0 | 1559.09 |
| 270–300 | 0.00 | 0.98 | 0 | 0 | 1560.00 |
| Total (gr) | 240.93 | 46.15 | 414.92 | 858 | 1560 |
| % Wt | 15.44 | 2.96 | 26.60 | 55.00 | 100 |
| % wt (t = 0) | 7.82 | 0.05 | 30.03 | 62.10 | 100 |

Density : VP: 1.04 g/ml
DMAPMA : 0.933 g/ml

EXAMPLE 4

Preparation of a Homogeneous Terpolymer of 55% VCL, 40% VP and 5% DMAPMA

Vinyl caprolactam (VCL) (511.5 g—100%), vinyl pyrrolidone (64.5 g—44.2%), DMAPMA (0.65 g—1.5%) and ethanol (858 g) were charged into a 2-liter resin pot equipped with a gas inlet, a liquid inlet, a thermometer and a condenser. The pH of the solution was adjusted to about 7.5 with KOH. Then a stream of nitrogen is introduced which bubbles through the solution during the reaction. The solution was gradually heated to 65° C. Then VP (63.2 g) and DMAPMA (51.4 g) were introduced incrementally into the pot with vigorous stirring over a period of 5 hours so that the relative concentrations of the monomeric VCL, VP and DMAPMA monomer remained practically constant throughout the reaction at predetermined levels.

TABLE 3

FEEDING SCHEDULE FOR EXAMPLE 4
Charge 45% solids in ethanol,
VP/DMAPMA/VCL = 25/5/70 (% mole)
Asymmetric Double Sigmoidal Distribution
VP (1, 7, 1, 34), DMAPMA (40, 20, 10, 80)

| Time (min) | VP (ml) | DMAPMA (ml) | VCL (gr) | EtOH (gr) | Total (gr) |
|---|---|---|---|---|---|
| 0 | 62.92 | 0.70 | 511.46 | 858.00 | 1435.55 |
| 0–30 | 40.98 | 6.34 | 0 | 0 | 1484.09 |
| 30–60 | 20.89 | 10.08 | 0 | 0 | 1515.22 |
| 60–90 | 9.56 | 8.50 | 0 | 0 | 1533.09 |
| 90–120 | 4.14 | 6.64 | 0 | 0 | 1543.58 |
| 120–150 | 1.75 | 5.03 | 0 | 0 | 1550.08 |
| 150–180 | 0.00 | 3.71 | 0 | 0 | 1553.55 |
| 180–210 | 0.00 | 2.69 | 0 | 0 | 1556.06 |
| 210–240 | 0.00 | 1.92 | 0 | 0 | 1557.85 |
| 240–270 | 0.00 | 1.36 | 0 | 0 | 1559.11 |
| 270–300 | 0.00 | 0.95 | 0 | 0 | 1560.00 |
| Total (gr) | 145.84 | 44.70 | 511.46 | 858 | 1560 |
| % Wt | 9.35 | 2.87 | 32.79 | 55.00 | 100 |
| % wt (t = 0) | 4.56 | 0.05 | 35.63 | 59.77 | 100 |

Density : VP: 1.04 g/ml
DMAPMA : 0.933 g/ml

Hair Care Compositions

In a water-based, rinse-off, hair styling and conditioning composition, the homogeneous terpolymer of the invention comprises about 0.2–20%, preferably 1–10%, and, most preferably, about 2–8%, by weight of the hair care product, the rest being water, and, optionally including an organic solvent such as ethanol, and/or other acceptable adjuvant components such as corrosion inhibitors, silicones, surface active agents, viscosity modifiers, dyes, chelating agents, distributing aids, pearlescent aids, opacifiers, perfumes, fatty alcohols, pH adjusting agents, and the like. Particularly desirable are corrosion inhibitors.

The homogeneous terpolymer of the invention also finds particular utility in multifunctional hair care products such as water-based, rinse-off hair styling and conditioning products, and in leave-on hair care products such as a mousse, and may be included as a concentrate, or as a gel, and applied as a self-actuated pump hair spray, or in an aerosol product with a propellant. Various actuator and packaging devices known in the art may be used therewith.

Procedure For Preparing Hair Spray Compositions of Invention

A. Pump Spray

The pump hair spray compositions of the invention were prepared by first dissolving the homogeneous terpolymer resin in ethanol and adding the requisite amount of water. The composition then was packaged into a high density polyethylene bottle fitted with a suitable pump actuator, e.g. a pump sprayer (160 ml) with 0.018×0.010 inch deep actuator (SEAQUIST EUROMIST II).

B. Aerosol Spray

The aerosol hair spray resin compositions of the invention were prepared from 65% by weight of the hair spray concentrate, a vapor phase inhibitor, a liquid phase inhibitor, adjuvants where needed, and 35% by weight of a propellant, e.g. dimethyl ether.

INVENTION EXAMPLES 5–8

The following hair spray compositions of the invention were prepared in a stainless steel mixing vessel and mixed at ambient temperature for 20 minutes with a turbine agitator.

TABLE 4

| HAIR SPRAY COMPOSITIONS | | | | |
|---|---|---|---|---|
| Example No. | 5 | 6 | 7 | 8 |
| Component | Weight % | | | |
| Homogeneous Terpolymer of Ex. 2 (45% active in ethanol) | 8.90 | 6.67 | 8.90 | 6.67 |
| Water | 41.00 | 42.00 | 40.50 | 41.50 |
| Adjuvants | | | 0.50 | 0.50 |
| Propellant | | | 35.00 | 35.00 |
| Ethanol | 50.10 | 51.33 | 15.10 | 16.33 |
| | 100.00 | 100.00 | 100.00 | 100.00 |

COMPARATIVE EXAMPLE 9

The following comparative hair spray composition was prepared in the manner set forth above.

TABLE 5

| EXAMPLE NO. 9 | |
|---|---|

TABLE 5-continued

| Component | Weight % |
|---|---|
| Non-Homogeneous Terpolymer of Ex. 1 (45% active in ethanol) | 8.90 |
| Water | 41.00 |
| Ethanol | 50.10 |

| HAIR SPRAY PROPERTIES INVENTION VS. COMPARATIVE EXAMPLE | | |
|---|---|---|
| | Homogeneous Composition (Ex. 5) | Non-Homogeneous Composition (Ex. 9) |
| Turbidity (HACH) | 0.6 | 40.1 |
| HHCR (90 min) | 88.6 | 84.2 |
| (4 hr.) | 76.6 | 75.3 |
| Particle size, DAV [V, 0.5] | 85.3 | 95.3 |
| Stiffness | 8.3 | 6.7 |
| Curl snap | 9.0 | 6.7 |
| Curl memory | 7.7 | 4.0 |

While the invention has been described with particular reference to certain embodiments thereof, it will be understood that changes and modifications may be made which are within the skill of the art. Accordingly, it is intended to be bound only by the following claims.

What is claimed is:

1. A homogeneous polymerization process for forming a clear solution of a hair fixative resin which is a homogeneous terpolymer of vinyl pyrrolidone (VP), vinyl caprolactam (VCL) and 3-(N-dimethylaminopropyl) methacrylamide (DMAPMA) monomers, in a compositional range of 60–95% VCL, 1–20% VP and 1–10% DMAPMA, by weight in alcohol or water, or mixtures thereof, at a solids content of 10–70%, having a clarity of less than 10 NTU, and a Brookfield viscosity of less than 300,000 cps, at a polymerization temperature of about 65° C., for about 5 hours, in the presence of a radical initiator at a pH of about 7.5, which consists essentially of the steps of:

(a) charging a reactor with VCL, optionally with an amount of VP and/or DMAPMA, and (b) introducing VP and DMAPMA incrementally into the reactor wherein the rate of disappearance of VCL, VP and DMAPMA are matched during the polymerization.

2. A process according to claim 1 wherein the homogeneous terpolymer comprises 80–90% VCL, 5–15% VP and 2.5–7.5% DMAPMA.

3. A process according to claim 1 wherein said solids content is 35–55%.

4. A process according to claim 1 wherein said clarity is less than 1 NTU.

5. A process according to claim 1 wherein up to about 50% of the total VP and up to about 10% of the total DMAPMA in said terpolymer is precharged.

6. A process according to claim 1 wherein the solvent is ethanol.

7. A hair fixative concentrate made by the process of claim 1.

8. A hair fixative concentrate made by the process of claim 2.

9. A hair fixative concentrate made by the process of claim 3.

10. A hair fixative concentrate made by the process of claim 4.

11. A 55% VOC pump hair spray composition comprising about 2–10 wt. % of the homogeneous terpolymer of claim 5, 55 wt. % or less of alcohol, and the rest water and adjuvants.

12. A 55% VOC pump hair spray composition according to claim 11 which comprises about 3–5 wt. % of the homogeneous terpolymer of claim 7.

13. A 55% VOC pump hair spray composition according to claim 11 which has a particle size of about 85 microns.

14. A 55% VOC pump hair spray composition according to claim 11 wherein said adjuvants includes one or more of a corrosion inhibitor, a surfactant, a neutralizing agent, a preservative, a hair conditioner, a hair curling agent, a hair coloring agent, and mixtures thereof.

15. A 55% VOC aerosol hair spray composition comprising about 1–10 wt. % of the homogeneous terpolymer of claim 7, 20 wt. % or less alcohol and 35 wt. % or less propellant, the rest water and adjuvants.

16. A 55% VOC aerosol hair spray composition according to claim 15 comprising about 2–4 wt. % of the homogeneous terpolymer.

17. A 55% VOC aerosol hair spray concentrate according to claim 14 wherein said adjuvants includes one or more of a corrosion inhibitor, a surfactant, a neutralizing agent, a preservative, a hair conditioner a hair curling agent, a hair coloring agent, and mixtures thereof.

* * * * *